US007892806B2

(12) United States Patent
Svendsen et al.

(10) Patent No.: US 7,892,806 B2
(45) Date of Patent: Feb. 22, 2011

(54) FUNGAL ALPHA-AMYLASE VARIANTS

(75) Inventors: Allan Svendsen, Horsholm (DK); Lars Beier, Lyngby (DK); Jesper Vind, Vaerlose (DK); Tina Spendler, Malov (DK); Morten Tovborg Jensen, Vaerlose (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/698,524

(22) Filed: Feb. 2, 2010

(65) Prior Publication Data

US 2010/0136655 A1 Jun. 3, 2010

Related U.S. Application Data

(63) Continuation of application No. 10/536,101, filed as application No. PCT/DK2004/000558 on Aug. 23, 2004, now abandoned.

(60) Provisional application No. 60/497,455, filed on Aug. 22, 2003.

(30) Foreign Application Priority Data

Aug. 22, 2003 (DK) .............................. 2003 01201

(51) Int. Cl.
*C12N 9/30* (2006.01)
*C12N 9/28* (2006.01)
*C12N 9/26* (2006.01)
*C12N 9/24* (2006.01)
*C12N 9/00* (2006.01)
*C12P 19/14* (2006.01)
*C12P 19/16* (2006.01)
*C12P 19/20* (2006.01)
*C07H 21/04* (2006.01)
*A21D 2/00* (2006.01)

(52) U.S. Cl. ....................... 435/203; 435/202; 435/201; 435/200; 435/183; 435/99; 435/98; 435/96; 426/20; 536/23.2

(58) Field of Classification Search ................. 435/203, 435/202, 201, 200, 183, 99, 98, 96; 426/20; 536/23.2
See application file for complete search history.

(56) References Cited

U.S. PATENT DOCUMENTS

| 5,989,169 | A | 11/1999 | Svendsen et al. |
| 6,162,628 | A | 12/2000 | Cherry et al. |
| 6,410,295 | B1 | 6/2002 | Andersen et al. |

FOREIGN PATENT DOCUMENTS

| RU | 2 176 452 | 12/2001 |
| WO | WO 96/23874 | 8/1996 |
| WO | WO 01/34784 | 5/2001 |
| WO | WO 03/012071 | * 2/2003 |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol.,2001, vol. 183 (8): 2405-2410.*
Whisstock et al., Prediction of protein function from protein sequence. Q. Rev. Biophysics., 2003, vol. 36 (3): 307-340.*
MacGregor et al., "Relationship of sequence and structure to specificity in the alpha-amylase family of enzymes", Biochimica et Biophysica Acta, pp. 1-20, (2001).
Svensson et al., "Protein engineering in the alpha-amylase family: catalytic mechanism, substrate specificity, and stability", Plant Molecular Biology, vol. 25, pp. 141-157, (1994).
Gyemant et al., "Subsite mapping of the binding region of alpha-amylases with a computer program", Eur. J. Biochem., vol. 269, pp. 5157-5162, (2002).
Mori et al., Eur. J. Biochem., vol. 269, pp. 5377-5390, (2002).
Zemla, Adam, Nucleic Acids Research, vol. 31, No. 13, pp. 3370-3374, (2003).
Lichtarge et al., J. Mol. Biol., vol. 257, pp. 342-358, (1996).
Bisgaard-Frantzen H.: "New Frontiers in alpha-amylase Contsruction" Starch-Starke, vol. 52, 2000, p. 310, XP002305404 Abstracts of the 51st Starch Convention 2000 at Detmold.
Bisgaard-Frantzen H.: "New Frontiers in Alpha-Amylase Engineering" Online! XP002305405, 2006, Retrieved from the Internet: URL WWW.AGFDT.DE/LOADS/ST00/BISGAARD.PDF> p. 4.
Beier et al., "Conversion of the Maltogenic Alpha-Amylase Novamyl Into a CGTase", Protein Engineering, vol. 13, No. 7 pp. 509-513, (2000).
Brzozowski, A. M., Davies, G. J.: Strauucture of the the *Aspergillus oryzae* alpha-amylase complexed with inhibitor acarbose at 2.0 A resolution. Biochem p. 10837-10845 (1997).
Boel et al., "Calcium binding in alpha-amylases: an X-ray diffraction study at 2.1-A resolution of two enzymes from *Aspergillus*", Biochemistry, vol. 29, p. 6244, (1990).
Swift et al., "Structure and molecular model refinement of *Aspergillus oryzae* (TAKA) alpha-amylase: an application of the simulated-annealing method" Acta Crystallogr. B 47, pp. 535, (1991).

(Continued)

*Primary Examiner* — Ganapathirama Raghu
(74) *Attorney, Agent, or Firm* — Kristin J. McNamara

(57) ABSTRACT

The inventors have developed a method of altering the amino acid sequence of a fungal alpha-amylase to obtain variants, and they have used the method to construct such variants. The variants may be useful for anti-staling in baked products. Accordingly, the invention provides a method of constructing fungal alpha-amylase variants based on a comparison of three-dimensional (3D) structures of the fungal alpha-amylase and a maltogenic alpha-amylase. One or both models includes a substrate. The invention also provides novel fungal alpha-amylase variants.

7 Claims, 2 Drawing Sheets

OTHER PUBLICATIONS

Brady et al, Structure Explorer-2AAA (1990).
Swift et al, Structure Explorer-6TAA (1991).
Davies et al, Structure Explorer -7TAA (1997).
Dauter et al, Biochemistry, vol. 38, pp. 8385-8392 (1999).
Alan Fersht, Enzyme Structure and Function, Book Second Edition 3 pages (1985).
Gilliland et al, Current Opinion in Structural Biology, vol. 6, pp. 595-603 (1996).
Ke et al, Methods, vol. 34, pp. 408-414 (2004).
Wieneck, New Strategies for Protein Crystal Growth, vol. 1, pp. 505-534 (1999).
Guo et al, PNAS, vol. 101, (25) pp. 9205-9210 (2004).
Witkowski et al, Biochemistry, vol. 38, pp. 11643-11650 (1999).
Wishart et al, Journal of Biology Chemistry, vol. 270, (45) pp. 26782-26785.
Kisselev et al, Structure, vol. 10, pp. 8-9 (2002).

* cited by examiner

```
SEQ ID NO: 2   ---------------------ATPADWRSQSIYFLLTDRFARTDGSTTATCNTADQKYCG
SEQ ID NO: 3   ---------------------LSAASWRTQSIYFLLTDRFGPTDNSTTATCNTGNEIYCG
SEQ ID NO: 4   ---------------------ATPDEWKAQSIYFMLTDRFARTDNSTTAPCDTTAGKYCG
                                    :. .*::*****:*****.***.****.*:*    ***

SEQ ID NO: 2   GTWQGIIDKLDYIQGMGFTAIWITPVTAQLPQTT--AYGDAYHGYWQQDIYSLNENYGTA
SEQ ID NO: 3   GSWQGIIDHLDYIEGNGFTAIWISPITEQLPQDT--ADGEAYHGYWQQKIYDVNSNFGTA
SEQ ID NO: 4   GTWRGIINNLDYIQDMGFTAIWITPVTAQWDDDVDAADAISYHGYWQKDLYSLNSKFGTA
               *:*:***::****:.**********:*:*  *   :.  * .:*****.::.:*.::***

SEQ ID NO: 2   DDLKALSSALHERGMYLMVDVVANHMGYDGAGSSVDYSVFKPFSSQDYFHPFCFIQNYED
SEQ ID NO: 3   DNLKSLSDALHARGMYLMVDVVPDEMGYACNGNDVDYCVFDPFDSSSYFHPYCLITDWDN
SEQ ID NO: 4   DDLKALADALHARGMLLMVDVVANHFGYGGSHSEVDYSIFNPLNSQDYFHPFCLIEDYDN
               *:**:*:.*** *** ******:.:** *   ..****:*.*:.*..****:*:* :::

SEQ ID NO: 2   QTQVEDCWLGDNTVSLPDLDTTKDVVKNEWYDWVGSLVSNYSIDGLRIDTVKHVQKDFWP
SEQ ID NO: 3   LTMVEDCWEGDTIVSLPDLTTTETAVRTIWYDWVADLVSNYGVDGLFIDSVLEVQPDFFP
SEQ ID NO: 4   QEEVEQCWLADTPTTLPDVDTTNPQVRTFNDWIKSLVANYSIDGLRVDTVKHVEKDFWP
                **:** .*. .:***:***:   *:.  :  **: .**:***:****:*:*  .*: **:*

SEQ ID NO: 2   GYNKAAGVYCIGEVLDGDPAYTCPYQNVMDGVLNYPIYYPLLNAFKSTSGSMDDLYNMIN
SEQ ID NO: 3   GYNKASGVYCVGEIDNGNPASDCPYQKVLDGVLNYPIYWQLDYAFECSSGSISNLYNMIK
SEQ ID NO: 4   DFNEAA-ACTVGEVFNGDPAYTCPYQEVLDGVLNYPIYYPALDAFKSVGGNLGGLAQAIT
                .:*:*:.   :**: :*:**  ****:*.:**********:    * **:* .*.:..* : *.

SEQ ID NO: 2   TVKSDCPDSTLLGTFVENHDNPRFASYTNDIALAKNVAAFIILNDGIPIIYAGQEQHYAG
SEQ ID NO: 3   SVASDCSDPTLLGNFIENIDNPRFAKYISDYSQAKNVLSYIFISDGIPIVYAGEEQHYAG
SEQ ID NO: 4   TVQESCKDSNLLGNFLENHDIARFASYTDDLALAKNGIAFIILSDGIPIIYTGQEQHYAG
               :*  ..* *..***.*:****  .***.**.* : ***  ::*:*.*****:*:*:******

SEQ ID NO: 2   GNDPANREATWLSGYPTDSELYKLIASAMAIRNYAISKDTGFVTYKNWPIYKDDTTIAMR
SEQ ID NO: 3   GKVPYNREATWLSGYDTSAELYTWIATTNAIRKLAIAADSAYITYANDAFYTDSNTIAMA
SEQ ID NO: 4   DHDPTNREAVWLSGYNTDAELYQFIKKANGIRNLAISQNPEFTSSKTKVIYQDDSTLAIN
                .: * ****:***** *.:***  *  .:.**: :  : .   :*  *..*:*:

SEQ ID NO: 2   KGTDGSQIVTILSNKGASGDSYTLSLSGAGYTAHQQLIEVIGCTTVTVGSDGNVPVPMAG
SEQ ID NO: 3   KGTSGSQVITVLSNKGSSGSSYIITLSGSGYTSVTKLIEAYTCTSVIVDSSGDIPVPMAS
SEQ ID NO: 4   RGG----VVTVLSNEGASGETGIVSIPGTGFEAGTELTDVISCKTVTAGDSGAVDVPLSG
                :*      ::*:***:*:**.: *:::.*:*: :* :*. :.  *.:**....* : **::.

SEQ ID NO: 2   GLPRVLYPTEKLAGSKICSSS------
SEQ ID NO: 3   GLPRVLLPASVVDSSSLCGGSGRLYVE
SEQ ID NO: 4   GLPSVLYPSSQLAKSGLCASA------
               *** ** *:. :  * :*..::
```

Figure 1

```
SSS--ASVKGDVIYQIIIDRFYDGDTTNNNPAKSYGLYD-----PTKSKWKMYWGGDLEGVRQKLP  59
A--TPADWRSQSIYFLLTDRFARTD--------------GSTTATCNTADQKYCGGTWQGIIDKLD 50
       ---  -                            ------
            -                             -----

YLKQLGVTTIWLSPVLDNLDTLAGTDNTGYHGYWTRDFKQIEEHFGNWTTFDTLVNDAHQNGIKVI 125
YIQGMGFTAIWITPVTAQLPQTTAY-GDAYHGYWQQDIYSLNENYGTADDLKALSSALHERGMYLM 116
   ----  -  -- ------  ---------                       -
                 --          ---- -

VDFVPNHSTP-FKANDSTFAE-GG-ALYNNGTYMGNYFDDATKGYFHHNGDISNWDDRYEAQWKNF 188
VDVVANHMGYDGAGSSV----DY-SVFKP----FSSQ------DYFHPFCFIQNYEDQTQVEDCWL 166
-----------                                -------  ---  -----
      --   --                              -- --               -

TDPA-GFSLADLSQENGTIAQYLTDAAVQLVA-HGADGLRIDAVKHFNSGFSKSLADKLYQKKDIF 252
GDNT-V-SLPDLDTTKDVVKNEWYDWVGSLVSNYSIDGLRIDTVKHVQKDFWPGYNKAAG----VY 226
-- -----                         --------          -              -
-- ---                                                   -

LVGEWYGDDPGTANHLEKVRYANNSGVNVLDFDLNTVIRNVFGTFTQTMYDLNNMVNQTGNEYKYK 318
CIGEVLDGDP-----AYTCPYQ-NVMDGVLNYPIYYPLLNAFKSTSGSMDDLYNMINIVKSDCPDS 286
-----------     -   -         -------------                -

ENLITFIDNHDMSRFLSVNSNKANLHQALAFILTSRGTPSIYYGTEQYMAGGNDPYNRGMM--PAF- 382
TLLGTFVENHDNPRFASYTNDIALAKNVAAFIILNDGIPIIYAGQEQHYAGGNDPANREATWLSGY 352
    - ------    -                       -             -------

DTTTTAFKEVSTLAGLRRNNA----AIQYGTTTQRWINNDVYIYERKFFNDVVLVAINRNT--QSS- 442
PTDSELYKLIASANAIRNYAISKDTGFVTYKNWPIYKDDTTIAMRKGTDGSQIVTILSNKGASGDS 418

YSISGLQTALPN-GSYADYLSGLLGGNGISVSNG-SVASFTLAPGAVSVWQY-----------STS 495
YTLSLSGAGYTAGQQLTEVIGC----TTVTVGS-DGNVPVPMAGGLPRVLYPTEKLAGSKICS--- 476

ASAPQIGSVAPNMGIPGNVVTIDGKGFGTTQGTVTFGGVTATVKSWTSNRIEVYVPNMAAGLTDVK 561
----------------------------------------------------------------

VTAGGVSSNLYSYNILSGTQTSVVFTVKSAPPTNLGDKIYLTGNIPELGNWSTDTSGAVNNAQGPL 627
----------------------------------------------------------------

LAPNYPDWFYVFSVPAGKTIQFKFFIKRADGTIQWENGSNHVATTPTGATGNITVIWQN  686
---------------------------------------------------------
```

Figure 2

```
SEQUENCE LISTING

<160> NUMBER OF SEQ ID NOS: 4

<210> SEQ ID NO 1
<211> LENGTH: 686
<212> TYPE: PRT
<213> ORGANISM: Bacillus stearothermophilus

<400> SEQUENCE: 1

Ser Ser Ser Ala Ser Val Lys Gly Asp Val Ile Tyr Gln Ile Ile Ile
1               5                   10                  15

Asp Arg Phe Tyr Asp Gly Asp Thr Thr Asn Asn Asn Pro Ala Lys Ser
            20                  25                  30

Tyr Gly Leu Tyr Asp Pro Thr Lys Ser Lys Trp Lys Met Tyr Trp Gly
        35                  40                  45

Gly Asp Leu Glu Gly Val Arg Gln Lys Leu Pro Tyr Leu Lys Gln Leu
    50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
            85                  90                  95

Phe Lys Gln Ile Glu Glu His Phe Gly Asn Trp Thr Thr Phe Asp Thr
        100                 105                 110

Leu Val Asn Asp Ala His Gln Asn Gly Ile Lys Val Ile Val Asp Phe
    115                 120                 125

Val Pro Asn His Ser Thr Pro Phe Lys Ala Asn Asp Ser Thr Phe Ala
130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
            165                 170                 175

Trp Asp Asp Arg Tyr Glu Ala Gln Trp Lys Asn Phe Thr Asp Pro Ala
        180                 185                 190

Gly Phe Ser Leu Ala Asp Leu Ser Gln Glu Asn Gly Thr Ile Ala Gln
    195                 200                 205
```

-continued

```
Tyr Leu Thr Asp Ala Ala Val Gln Leu Val Ala His Gly Ala Asp Gly
    210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Thr Ala Asn His Leu Glu Lys Val Arg
                260                 265                 270

Tyr Ala Asn Asn Ser Gly Val Asn Val Leu Asp Phe Asp Leu Asn Thr
                275                 280                 285

Val Ile Arg Asn Val Phe Gly Thr Phe Thr Gln Thr Met Tyr Asp Leu
    290                 295                 300

Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Ser Val
                325                 330                 335

Asn Ser Asn Lys Ala Asn Leu His Gln Ala Leu Ala Phe Ile Leu Thr
                340                 345                 350

Ser Arg Gly Thr Pro Ser Ile Tyr Tyr Gly Thr Glu Gln Tyr Met Ala
                355                 360                 365

Gly Gly Asn Asp Pro Tyr Asn Arg Gly Met Met Pro Ala Phe Asp Thr
370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Thr Gln Arg Trp Ile Asn
                405                 410                 415

Asn Asp Val Tyr Ile Tyr Glu Arg Lys Phe Phe Asn Asp Val Val Leu
                420                 425                 430

Val Ala Ile Asn Arg Asn Thr Gln Ser Ser Tyr Ser Ile Ser Gly Leu
            435                 440                 445

Gln Thr Ala Leu Pro Asn Gly Ser Tyr Ala Asp Tyr Leu Ser Gly Leu
    450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Ser Ala
                485                 490                 495

Ser Ala Pro Gln Ile Gly Ser Val Ala Pro Asn Met Gly Ile Pro Gly
                500                 505                 510

Asn Val Val Thr Ile Asp Gly Lys Gly Phe Gly Thr Thr Gln Gly Thr
            515                 520                 525

Val Thr Phe Gly Gly Val Thr Ala Thr Val Lys Ser Trp Thr Ser Asn
    530                 535                 540

Arg Ile Glu Val Tyr Val Pro Asn Met Ala Ala Gly Leu Thr Asp Val
545                 550                 555                 560

Lys Val Thr Ala Gly Gly Val Ser Ser Asn Leu Tyr Ser Tyr Asn Ile
                565                 570                 575

Leu Ser Gly Thr Gln Thr Ser Val Val Phe Thr Val Lys Ser Ala Pro
                580                 585                 590

Pro Thr Asn Leu Gly Asp Lys Ile Tyr Leu Thr Gly Asn Ile Pro Glu
            595                 600                 605

Leu Gly Asn Trp Ser Thr Asp Thr Ser Gly Ala Val Asn Asn Ala Gln
    610                 615                 620

Gly Pro Leu Leu Ala Pro Asn Tyr Pro Asp Trp Phe Tyr Val Phe Ser
```

```
                625                 630                 635                 640
Val Pro Ala Gly Lys Thr Ile Gln Phe Lys Phe Ile Lys Arg Ala
                    645                 650                 655

Asp Gly Thr Ile Gln Trp Glu Asn Gly Ser Asn His Val Ala Thr Thr
                660                 665                 670

Pro Thr Gly Ala Thr Gly Asn Ile Thr Val Thr Trp Gln Asn
        675                 680                 685

<210> SEQ ID NO 2
<211> LENGTH: 478
<212> TYPE: PRT
<213> ORGANISM: Aspergillus oryzae

<400> SEQUENCE: 2

Ala Thr Pro Ala Asp Trp Arg Ser Gln Ser Ile Tyr Phe Leu Leu Thr
1               5                   10                  15

Asp Arg Phe Ala Arg Thr Asp Gly Ser Thr Thr Ala Thr Cys Asn Thr
            20                  25                  30

Ala Asp Gln Lys Tyr Cys Gly Gly Thr Trp Gln Gly Ile Ile Asp Lys
        35                  40                  45

Leu Asp Tyr Ile Gln Gly Met Gly Phe Thr Ala Ile Trp Ile Thr Pro
    50                  55                  60

Val Thr Ala Gln Leu Pro Gln Thr Thr Ala Tyr Gly Asp Ala Tyr His
65                  70                  75                  80

Gly Tyr Trp Gln Gln Asp Ile Tyr Ser Leu Asn Glu Asn Tyr Gly Thr
                85                  90                  95

Ala Asp Asp Leu Lys Ala Leu Ser Ser Ala Leu His Glu Arg Gly Met
            100                 105                 110

Tyr Leu Met Val Asp Val Val Ala Asn His Met Gly Tyr Asp Gly Ala
        115                 120                 125

Gly Ser Ser Val Asp Tyr Ser Val Phe Lys Pro Phe Ser Ser Gln Asp
    130                 135                 140

Tyr Phe His Pro Phe Cys Phe Ile Gln Asn Tyr Glu Asp Gln Thr Gln
145                 150                 155                 160

Val Glu Asp Cys Trp Leu Gly Asp Asn Thr Val Ser Leu Pro Asp Leu
                165                 170                 175

Asp Thr Thr Lys Asp Val Val Lys Asn Glu Trp Tyr Asp Trp Val Gly
            180                 185                 190

Ser Leu Val Ser Asn Tyr Ser Ile Asp Gly Leu Arg Ile Asp Thr Val
        195                 200                 205

Lys His Val Gln Lys Asp Phe Trp Pro Gly Tyr Asn Lys Ala Ala Gly
    210                 215                 220

Val Tyr Cys Ile Gly Glu Val Leu Asp Gly Asp Pro Ala Tyr Thr Cys
225                 230                 235                 240

Pro Tyr Gln Asn Val Met Asp Gly Val Leu Asn Tyr Pro Ile Tyr Tyr
                245                 250                 255

Pro Leu Leu Asn Ala Phe Lys Ser Thr Ser Gly Ser Met Asp Asp Leu
            260                 265                 270

Tyr Asn Met Ile Asn Thr Val Lys Ser Asp Cys Pro Asp Ser Thr Leu
        275                 280                 285

Leu Gly Thr Phe Val Glu Asn His Asp Asn Pro Arg Phe Ala Ser Tyr
    290                 295                 300

Thr Asn Asp Ile Ala Leu Ala Lys Asn Val Ala Ala Phe Ile Ile Leu
305                 310                 315                 320
```

```
Asn Asp Gly Ile Pro Ile Ile Tyr Ala Gly Gln Glu Gln His Tyr Ala
                325             330                 335

Gly Gly Asn Asp Pro Ala Asn Arg Glu Ala Thr Trp Leu Ser Gly Tyr
            340                 345                 350

Pro Thr Asp Ser Glu Leu Tyr Lys Leu Ile Ala Ser Ala Asn Ala Ile
            355                 360                 365

Arg Asn Tyr Ala Ile Ser Lys Asp Thr Gly Phe Val Thr Tyr Lys Asn
    370                 375                 380

Trp Pro Ile Tyr Lys Asp Asp Thr Thr Ile Ala Met Arg Lys Gly Thr
385                 390                 395                 400

Asp Gly Ser Gln Ile Val Thr Ile Leu Ser Asn Lys Gly Ala Ser Gly
                405                 410                 415

Asp Ser Tyr Thr Leu Ser Leu Ser Gly Ala Gly Tyr Thr Ala Gly Gln
                420                 425                 430

Gln Leu Thr Glu Val Ile Gly Cys Thr Thr Val Thr Val Gly Ser Asp
            435                 440                 445

Gly Asn Val Pro Val Pro Met Ala Gly Gly Leu Pro Arg Val Leu Tyr
    450                 455                 460

Pro Thr Glu Lys Leu Ala Gly Ser Lys Ile Cys Ser Ser Ser
465                 470                 475

<210> SEQ ID NO 3
<211> LENGTH: 476
<212> TYPE: PRT
<213> ORGANISM: Aspergillus niger

<400> SEQUENCE: 3

Leu Ser Ala Ala Ser Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
            20                  25                  30

Gly Asn Glu Ile Tyr Cys Gly Gly Ser Trp Gln Gly Ile Ile Asp His
            35                  40                  45

Leu Asp Tyr Ile Glu Gly Met Gly Phe Thr Ala Ile Trp Ile Ser Pro
50                  55                  60

Ile Thr Glu Gln Leu Pro Gln Asp Thr Ala Asp Gly Glu Ala Tyr His
65                  70                  75                  80

Gly Tyr Trp Gln Gln Lys Ile Tyr Asp Val Asn Ser Asn Phe Gly Thr
            85                  90                  95

Ala Asp Asn Leu Lys Ser Leu Ser Asp Ala Leu His Ala Arg Gly Met
            100                 105                 110

Tyr Leu Met Val Asp Val Val Pro Asp His Met Gly Tyr Ala Gly Asn
            115                 120                 125

Gly Asn Asp Val Asp Tyr Ser Val Phe Asp Pro Phe Asp Ser Ser Ser
    130                 135                 140

Tyr Phe His Pro Tyr Cys Leu Ile Thr Asp Trp Asp Asn Leu Thr Met
145                 150                 155                 160

Val Glu Asp Cys Trp Glu Gly Asp Thr Ile Val Ser Leu Pro Asp Leu
            165                 170                 175

Asp Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
            195                 200                 205

Leu Glu Val Gln Pro Asp Phe Phe Pro Gly Tyr Asn Lys Ala Ser Gly
    210                 215                 220
```

-continued

```
Val Tyr Cys Val Gly Glu Ile Asp Asn Gly Asn Pro Ala Ser Asp Cys
225                 230                 235                 240

Pro Tyr Gln Lys Val Leu Asp Gly Val Leu Asn Tyr Pro Ile Tyr Trp
            245                 250                 255

Gln Leu Leu Tyr Ala Phe Glu Ser Ser Ser Gly Ser Ile Ser Asn Leu
            260                 265                 270

Tyr Asn Met Ile Lys Ser Val Ala Ser Asp Cys Ser Asp Pro Thr Leu
            275                 280                 285

Leu Gly Asn Phe Ile Glu Asn His Asp Asn Pro Arg Phe Ala Lys Tyr
            290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Glu Gln His Tyr Ala
                325                 330                 335

Gly Gly Lys Val Pro Tyr Asn Arg Glu Ala Thr Trp Leu Ser Gly Tyr
            340                 345                 350

Asp Thr Ser Ala Glu Leu Tyr Thr Trp Ile Ala Thr Asn Ala Ile
            355                 360                 365

Arg Lys Leu Ala Ile Ala Ala Asp Ser Ala Tyr Ile Thr Tyr Ala Asn
            370                 375                 380

Asp Ala Phe Tyr Thr Asp Ser Asn Thr Ile Ala Met Ala Lys Gly Thr
385                 390                 395                 400

Ser Gly Ser Gln Val Ile Thr Val Leu Ser Asn Lys Gly Ser Ser Gly
                405                 410                 415

Ser Ser Tyr Thr Leu Thr Leu Ser Gly Ser Gly Tyr Thr Ser Gly Thr
            420                 425                 430

Lys Leu Ile Glu Ala Tyr Thr Cys Thr Ser Val Thr Val Asp Ser Ser
            435                 440                 445

Gly Asp Ile Pro Val Pro Met Ala Ser Gly Leu Pro Arg Val Leu Leu
            450                 455                 460

Pro Ala Ser Val Val Asp Ser Ser Ser Leu Cys Gly
465                 470                 475
```

<210> SEQ ID NO 4
<211> LENGTH: 475
<212> TYPE: PRT
<213> ORGANISM: Thermomyces lanuginosus

<400> SEQUENCE: 4

```
Ala Thr Pro Asp Glu Trp Lys Ala Gln Ser Ile Tyr Phe Met Leu Thr
1               5                   10                  15

Asp Arg Phe Ala Arg Thr Asp Asn Ser Thr Thr Ala Pro Cys Asp Thr
            20                  25                  30

Thr Ala Gly Lys Tyr Cys Gly Gly Thr Trp Arg Gly Ile Ile Asn Asn
            35                  40                  45

Leu Asp Tyr Ile Gln Asp Met Gly Phe Thr Ala Ile Trp Ile Thr Pro
50                  55                  60

Val Thr Ala Gln Trp Asp Asp Val Asp Ala Asp Ala Thr Ser
65                  70                  75                  80

Tyr His Gly Tyr Trp Gln Lys Asp Leu Tyr Ser Leu Asn Ser Lys Phe
            85                  90                  95

Gly Thr Ala Asp Asp Leu Lys Ala Leu Ala Asp Ala Leu His Ala Arg
            100                 105                 110

Gly Met Leu Leu Met Val Asp Val Val Ala Asn His Phe Gly Tyr Gly
```

-continued

```
                    115                 120                 125
Gly Ser His Ser Glu Val Asp Tyr Ser Ile Phe Asn Pro Leu Asn Ser
        130                 135                 140
Gln Asp Tyr Phe His Pro Phe Cys Leu Ile Glu Asp Tyr Asp Asn Gln
145                 150                 155                 160
Glu Glu Val Glu Gln Cys Trp Leu Ala Asp Thr Pro Thr Thr Leu Pro
                165                 170                 175
Asp Val Asp Thr Thr Asn Pro Gln Val Arg Thr Phe Phe Asn Asp Trp
                180                 185                 190
Ile Lys Ser Leu Val Ala Asn Tyr Ser Ile Asp Gly Leu Arg Val Asp
        195                 200                 205
Thr Val Lys His Val Glu Lys Asp Phe Trp Pro Asp Phe Asn Glu Ala
        210                 215                 220
Ala Ala Cys Thr Val Gly Glu Val Phe Asn Gly Asp Pro Ala Tyr Thr
225                 230                 235                 240
Cys Pro Tyr Gln Glu Val Leu Asp Gly Val Leu Asn Tyr Pro Ile Tyr
                245                 250                 255
Tyr Pro Ala Leu Asp Ala Phe Lys Ser Val Gly Gly Asn Leu Gly Gly
                260                 265                 270
Leu Ala Gln Ala Ile Thr Thr Val Gln Glu Ser Cys Lys Asp Ser Asn
        275                 280                 285
Leu Leu Gly Asn Phe Leu Glu Asn His Asp Ile Ala Arg Phe Ala Ser
        290                 295                 300
Tyr Thr Asp Asp Leu Ala Leu Ala Lys Asn Gly Leu Ala Phe Ile Ile
305                 310                 315                 320
Leu Ser Asp Gly Ile Pro Ile Ile Tyr Thr Gly Gln Glu Gln His Tyr
                325                 330                 335
Ala Gly Asp His Asp Pro Thr Asn Arg Glu Ala Val Trp Leu Ser Gly
                340                 345                 350
Tyr Asn Thr Asp Ala Glu Leu Tyr Gln Phe Ile Lys Lys Ala Asn Gly
        355                 360                 365
Ile Arg Asn Leu Ala Ile Ser Gln Asn Pro Glu Phe Thr Ser Ser Lys
        370                 375                 380
Thr Lys Val Ile Tyr Gln Asp Asp Ser Thr Leu Ala Ile Asn Arg Gly
385                 390                 395                 400
Gly Val Val Thr Val Leu Ser Asn Glu Gly Ala Ser Gly Glu Thr Gly
                405                 410                 415
Thr Val Ser Ile Pro Gly Thr Gly Phe Glu Ala Gly Thr Glu Leu Thr
                420                 425                 430
Asp Val Ile Ser Cys Lys Thr Val Thr Ala Gly Asp Ser Gly Ala Val
                435                 440                 445
Asp Val Pro Leu Ser Gly Gly Leu Pro Ser Val Leu Tyr Pro Ser Ser
        450                 455                 460
Gln Leu Ala Lys Ser Gly Leu Cys Ala Ser Ala
465                 470                 475
```

FUNGAL ALPHA-AMYLASE VARIANTS

CROSS-REFERENCE TO RELATED APPLICATIONS

This application is a continuation of U.S. application Ser. No. 10/536,101 filed on Feb. 22, 2005 (now abandoned), which is a 35 U.S.C. 371 national application of PCT/DK2004/000558 filed Aug. 23, 2004, which claims priority or the benefit under 35 U.S.C. 119 of Danish Application No. PA 2003 01201 filed Aug. 22, 2003 and U.S. Provisional Application No. 60/497,455 filed Aug. 22, 2003, the contents of which are fully incorporated herein by reference.

FIELD OF THE INVENTION

The present invention relates to the construction of variants of fungal alpha-amylases.

BACKGROUND OF THE INVENTION

WO 0134784 discloses variants of a fungal alpha-amylase. Pdb files 2AAA, 6taa and 7taa (available at rcsb.org) show the amino acid sequences and three-dimensional structures of fungal alpha-amylases. WO 9943794 discloses the amino acid sequence and three-dimensional structure of a maltogenic alpha-amylase from *Bacillus stearothermophilus*, known as Novamyl®.

SUMMARY OF THE INVENTION

The inventors have developed a method of altering the amino acid sequence of a fungal alpha-amylase to obtain variants with improved anti-staling effect and a higher degree of exo-amylase activity (increased ratio of exo-amylase to endo-amylase), and they have used the method to construct such variants. The variants may be useful for anti-staling in baked products.

Accordingly, the invention provides a method of constructing fungal alpha-amylase variants based on a comparison of three-dimensional (3D) structures of the fungal alpha-amylase and a maltogenic alpha-amylase. One or both models includes a substrate. The invention also provides novel fungal alpha-amylase variants and use of the variants in the preparation of dough and baked products.

BRIEF DESCRIPTION OF DRAWINGS

FIG. 1 shows an alignment of fungal amylases SEQ ID NO: 2, 3 and 4.

FIG. 2 shows an alignment of the 3D structures 1QHO for the maltogenic alpha-amylase Novamyl (SEQ ID NO: 1) at top and 6taa for a fungal alpha-amylase (SEQ ID NO: 2) below. Details are described in Example 1.

DETAILED DESCRIPTION OF THE INVENTION

Fungal alpha-amylase

The method of the invention uses an amino acid sequence of a fungal alpha-amylase and a three-dimensional model for the fungal alpha-amylase. The model may include a substrate.

The fungal alpha-amylase may be one of the following having the indicated amino acid sequence and a three-dimensional structure found under the indicated identifier in the Protein Data Bank (available at rcsb.org): acid alpha-amylase from *Aspergillus niger* (2AAA, SEQ ID NO: 3), alpha-amylase (Taka amylase) from *Aspergillus oryzae* (6taa or 7taa, SEQ ID NO: 2) or alpha-amylase from *Thermomyces lanuginosus* (SEQ ID NO: 4, WO 9601323). Alternatively, the fungal alpha-amylase may be a variant having at least 70% amino acid identity with SEQ ID NO: 2, e.g. a variant described in WO 0134784.

3D structures for other fungal alpha-amylases may be constructed as described in Example 1 of WO 9623874. To develop variants of a fungal alpha-amylase without a known 3D structure, the sequence may be aligned with a fungal alpha-amylase having a known 3D structure. The sequence alignment may be done by conventional methods, e.g. by use the software GAP from UWGCG Version 8. FIG. 1 shows an alignment of SEQ ID NO: 4 (without a known 3D structure) with SEQ ID NO: 2 and 3 (with known structures).

Maltogenic alpha-amylase

The method also uses an amino acid sequence of a maltogenic alpha-amylase (EC 3.2.1.133) and a three-dimensional model of the maltogenic alpha-amylase. The model may include a substrate. The maltogenic alpha-amylase may have the amino acid sequence have the amino acid sequence shown in SEQ ID NO: 1 (in the following referred to as Novamyl). A 3D model for Novamyl with a substrate is described in U.S. Pat. No. 6,162,628 and is found in the Protein Data Bank with the identifier 1QHO. Alternatively, the maltogenic alpha-amylase may be a Novamyl variant described in U.S. Pat. No. 6,162,628. A 3D structure of such a variant may be developed from the Novamyl structure by known methods, e.g. as described in T. L. Blundell et al., Nature, vol. 326, p. 347 ff (26 Mar. 1987); J. Greer, Proteins: Structure, Function and Genetics, 7:317-334 (1990); or Example 1 of WO 9623874.

Superimposition of 3D Models

The two 3D models may be superimposed by aligning the amino acid residues of each catalytic triad by methods known in the art. This may be based on the deviations of heavy atoms (i.e. non-hydrogen atoms) in the active sites, e.g. by minimizing the sum of squares of deviations. Alternatively, the superimposition may be based on the deviations of the three pairs of C-alpha atoms, e.g. by minimizing the sum of squares of the three deviations or by aligning so as to keep each deviation below 0.8 Å, e.g. below 0.6 Å, below 0.4 Å, below 0.3 Å or below 0.2 Å.

The structural alignment may be done by use of known software. In the structurally aligned models, pairs of residues from different sequences are considered to be aligned when they are located close to each other. The following software may be used:

DALI software, available at ebi.ac.uk/dali.

CE software available at cl.sdsc.edu.

STAMP software available at compbio.dundee.ac.uk/Software/Stamp/stamp.html.

Protein 3Dhome at lecb.ncifcrf.gov/~tsai.

Yale Gernstein Lab—spare parts at bioinfo.mbb.yale.edu/align.

Structural alignment server at molmovdb.org/align.

Substrate

A 3D structure of the enzyme(s) having a substrate or substrate analog in the active site binding cleft. A "substrate" could be a substrate bound in an inactive or active enzyme, or a substrate inhibitor like acarbose bound in the active site, or a modelled substrate in the active site, a docked substrate in the active site, or a substrate superimposed into the enzyme of interest and taken from a homologous 3D structure having such substrate or substrate analog bound in the active site.

Selection of Amino Acid Residues

In the superimposed 3D models, amino acid residues in the fungal alpha-amylase sequence are selected by two criteria: Firstly, fungal alpha-amylase residues <11 Å from a substrate (i.e. residues having a C-alpha atom located <11 Å from an atom of a substrate) are selected. Secondly, fungal alpha-amylase residues >0.8 Å from any maltogenic alpha-amylase residue (i.e. fungal alpha-amylase residues having a C-alpha atom >0.8 Å from the C-alpha atom of any maltogenic alpha-amylase residue) are selected.

Alteration of Fungal Alpha-Amylase Amino Acid Sequence

One or more of the following alterations are made to the fungal alpha-amylase sequence:

Deletion or Substitution

A fungal alpha-amylase residue <11 Å from a substrate and >0.8 Å from any maltogenic alpha-amylase residue may be deleted or may be substituted with a different residue.

The substitution may be made with the same amino acid residue as found at a corresponding position in the maltogenic alpha-amylase sequence or with a residue of the same type. The type indicates a positively charged, negatively charged, hydrophilic or hydrophobic residue, understood as follows (Tyr may be hydrophilic or hydrophobic):

Hydrophobic amino acids: Ala, Val, Leu, Ile, Pro, Phe, Trp, Gly, Met, Tyr

Hydrophilic amino acids: Thr, Ser, Gln, Asn, Tyr, Cys

Positively charged amino acids: Lys, Arg, His

Negatively charged amino acids: Glu, Asp

The fungal alpha-amylase residue may be substituted with a larger or smaller residue depending on whether a larger or smaller residue is found at a corresponding position in the maltogenic alpha-amylase sequence. In this connection, the residues are ranked as follows from smallest to largest: (an equal sign indicates residues with sizes that are practically indistin-guishable):

G<A=S=C<V=T<P<L=I=N=D=M<E=Q<K<H<R=F<Y<W

Insertion

One or more amino acid residues may be inserted at a position in the fungal alpha-amylase sequence corresponding to one or more residues in the maltogenic alpha-amylase sequence which are <11 Å from a substrate and which are >0.8 Å from any fungal alpha-amylase residue. The insertion may be made with the same residue as in the maltogenic alpha-amylase sequence or with another amino acid residue of the same type. The type indicates a positively charged, negatively charged, hydrophilic or hydrophobic residue, as above.

Where the maltogenic alpha-amylase sequence contains a consecutive stretch (a peptide loop) of residues which are >0.8 Å from any fungal alpha-amylase residue and of which some are <11 Å from a substrate, the insertion at the corresponding position in the fungal alpha-amylase sequence may consist of an equal number of residues, or the insertion may have one or two fewer or more residues. Thus, in the case of a stretch of 5 such residues in the maltogenic alpha-amylase sequence, the insertion may be made with 3-7 residues, e.g. 3, 4, 5, 6 or 7 residues. Each inserted residue may be the same as one of the maltogenic alpha-amylase residues or of the same type.

Optional Further Alterations of the Fungal Alpha-Amylase Sequence

Optionally, one or more other residues in the fungal alpha-amylase sequence may be substituted. The substitution may be made as described in WO 0134784 and may improve the thermostability of the variant.

A fungal alpha-amylase residue <11 Å of a substrate and <0.8 Å of a maltogenic alpha-amylase residue may be substituted with a residue identical to or of the same type as the corresponding maltogenic alpha-amylase residue, or with a larger or smaller residue depending on whether the corresponding maltogenic alpha-amylase residue is larger or smaller.

Degree of Exo-Activity

The degree of exo amylase activity is given as a relative activity compared to the endo amylase activity. The endo activity can be measured by a number of well known assays e.g. starch iodine, Phadebas (Amersham now GE Healthcare), or AZCL-amylose (Megazyme). The exo activity is preferably a measure of the small malto-oligomers released from starch at initial phases of hydrolysis. It is preferably measured by total carbohydrate after removal of the remaining starch, by the exo activity assay described below or similar method, but could be measured by other means e.g. the sum of oligomers by HPAEC-PAD (Dionex) or sum of oligomers after size exclusion chromatography.

Endo-Amylase Activity Assay:

1 mL resuspended Phadebas substrate (0.25 tablets/mL 50 mM sodium acetate, 1 mM $CaCl_2$, adjusted to pH 5.7) is incubated with 25 micro-L enzyme for 15 min at 40° C. with agitation. The reaction is stopped by addition of 0.5 mL 1 M NaOH and the mixture is centrifuged in a table centrifuge at 14,000 RPM. The absorbance of the supernatant at 620 nm is measured. The activity is determined by comparing to a standard with declared activity (BAN 480 L, 480 KNU/g)

Exo-Amylase Activity Assay:

900 µL 3.3% solubilized waxy maize starch (3.3% starch is boiled in 50 mM sodium acetate, 1 mM $CaCl_2$, pH 5.7 for 5 min and cooled to 40° C.) is incubated with 100 micro-L enzyme at 40° C. with stirring. After appropriate reaction time the remaining starch is precipitated by addition of 450 micro-L 4° C. 96% ethanol. The precipitate is immediately removed by centrifugation at 3000 G for 20 min. The total carbohydrate in the supernatant is determined by mixing 200 micro-L supernatant with 50 micro-L 2% tryptophan and 900 micro-L 64% sulfuric acid. The mixture is heated for 15 min at 95° C. and the absorbance at 630 nm is measured after cooling to room temperature. The activity is determined by comparing with the absorbance of glucose standards in the same assay. One unit is defined as the amount of enzyme that at initial rates liberates 1 mg oligomeric products (products that are not precipitated by ethanol) per min.

Fungal Alpha-Amylase Variants

A fungal alpha-amylase variant may be a polypeptide which:

a) has an amino acid sequence having at least 70% identity to SEQ ID NO: 2, 3 or 4; and b) comprises an amino acid alteration which is deletion, substitution or insertion as described below, and c) has the ability to hydrolyze starch.

The identity may be at least 80%, at least 90% or at least 95%. Amino acid identity may be determined as described in U.S. Pat. No. 6,162,628.

Production of Fungal Alpha-Amylase Variants

A polypeptide having the resulting amino acid sequence may be produced by conventional methods, generally involving producing DNA with a sequence encoding the polypeptide together with control sequences, transforming a suitable host organism with the DNA, cultivating the transformed organism at suitable conditions for expressing and optionally secreting the polypeptide, and optionally recovering the expressed polypeptide.

DNA encoding any of the above fungal alpha-amylase variants may be prepared, e.g. by point-specific mutation of DNA encoding the parent fungal alpha-amylase. This may be followed by transformation of a suitable host organism with the DNA, and cultivation of the transformed host organism under suitable conditions to express the encoded polypeptide (fungal alpha-amylase variant). This may be done by known methods.

Optional Screening of Fungal Alpha-Amylase Variants

Optionally, one or more expressed polypeptides may be tested for useful properties. This may include testing for the ability to hydrolyze starch or a starch derivative by a conventional method, e.g. a plate assay, use of Phadebas tablets or DSC on amylopectin. Also, the polypeptide may be tested for thermostability, and a more thermostable one may be preferred. Finally, the polypeptide may be tested by adding it to a dough, baking it and testing the firmness of the baked product during storage; a polypeptide with anti-staling effect may be selected as described in WO 9104669 or U.S. Pat. No. 6,162,628.

Optional Gene Recombination

Optionally, DNA encoding a plurality of the above fungal alpha-amylase variants may be prepared and recombined, followed by transformation of a suitable host organism with the recombined DNA, and cultivation of the transformed host organism under suitable conditions to express the encoded polypeptides (fungal alpha-amylase variants). The gene recombination may be done by known methods.

Dough and Baked Product

The variants are useful in the preparation of dough and baked products from dough. Particularly, the variant may be added in an amount which is effective to retard the staling of the baked product.

The dough may be leavened e.g. by adding chemical leavening agents or yeast, usually *Saccharomyces cerevisiae* (baker's yeast). The dough generally comprises flour, particularly wheat flour. Examples of baked products are bread and rolls.

The dough may comprise an additional enzyme, e.g. a second amylase, a protease or peptidase, a transglutaminase, a lipolytic enzyme, a cellulase, a xylanase or an oxidoreductase, e.g. a carbohydrate oxidase with activity on glucose and/or maltose. The lipolytic enzyme may have triacyl glycerol lipase activity, phospholipase activity and/or galactolipase activity, e.g. as described in WO 9953769, WO 9826057 or WO 0032758.

EXAMPLES

Example 1

Construction of Variants of Fungal Alpha-Amylase from *A. oryzae*

Two 3D structures with substrates were used: 6taa for a fungal alpha-amylase (SEQ ID NO: 2) and 1QHO for a maltogenic alpha-amylase (Novamyl, SEQ ID NO: 1), wherein the substrates are indicated as ABC for 6taa and as ABD for 1QHO. The two structures were superimposed using the heavy atoms of the three C-alpha atoms at the catalytic triad: D206, E230 and D297 for 6taa, and D228, E256 and D329 for Novamyl. The superimposed structures were analyzed, and the result is shown in FIG. 2 with the Novamyl sequence at the top and the fungal alpha-amylase sequence below.

The following fungal alpha-amylase residues were found to have a C-alpha atom <11 Å from an atom of either substrate: 13, 14, 15, 18, 31, 32, 33, 34, 35, 36, 61, 62, 63,64, 66, 68, 69, 71, 72, 73, 74, 75, 76, 77, 78, 79, 80, 81, 82, 83, 84, 94, 117,118, 119, 120, 121, 122, 123, 124,125, 126, 127, 151, 152, 153, 154, 155, 156, 157, 158, 160,161, 162, 164, 165, 166, 167,168, 169, 170, 171, 172, 173, 174, 175, 204,205, 206, 207, 208, 209, 210, 211,216,228, 229,230, 231, 232, 233, 234, 235, 236, 237, 238, 239,242, 250,251, 252, 253, 254, 255, 256,257, 258, 259, 260, 275, 292, 294,295, 296, 297, 298, 299, 304, 328, 338, 239, 340, 341, 342, 343, 344. They are indicated by the first underlining in FIG. 2.

The following fungal alpha-amylase residues were found to be included in either of the above subsets (<11 Å from a substrate or in a loop) and to have a C-alpha atom >0.8 Å from the C-alpha atom of any Novamyl residue: 15, 32, 33, 34, 35, 36, 63, 64, 73, 74, 75, 76, 77, 119, 120, 125, 126, 151, 152, 155, 156, 167, 168, 169, 170, 171, 172, 211, 233, 234, 235, 236, 237, 238, 239. They are indicated by the second underlining in FIG. 2.

Variants were constructed by substituting a selected residue in SEQ ID NO: 2 (fungal amylase) as indicated below:

| Selected residue in SEQ ID NO: 2 (fungal amylase) | Corresponding residue in SEQ ID NO: 1 (Novamyl) | Criteria for substitution | Particular substitution in SEQ ID NO: 2 |
|---|---|---|---|
| Q35 | K44 | larger and/or positive | Q35K/R |
| Y75 | T84 | smaller | Y75A/F |
| Y155 | W177 | larger and/or hydrophobic | Y155W |
| L166 | F188 | larger and/or hydrophobic | L166F |
| G167 | T189 | larger and/or hydrophilic | G167T |
| N169 | P191 | smaller and/or hydrophobic | N169P |
| T170 | A192 | smaller and/or hydrophobic | T170A |
| L232 | Y258 | larger | L232Y |
| D233 | G259 | smaller and/or hydrophobic | D233G |
| G234 | D260 | larger and/or negative | G234D |
| Y252 | F284 | smaller and/or hydrophobic | Y252F |
| Y256 | T288 | smaller and/or hydrophilic | Y256T |

Variants were constructed by altering a subsequence with insertion of an additional residue in SEQ ID NO: 2 (fungal amylase) to match the number of residues in SEQ ID NO: 1, as indicated below:

| Alteration In SEQ ID NO: 2 (fungal amylase) |
|---|
| 166LGDNTV171 to FTDPAGF (Novamyl loop (long)) |
| 168-171 (DNTV) substituted with DPAGF (Novamyl loop) |
| 168-171 (DNTV) substituted with DPAGL (Novamyl loop with adjustments in last part) |
| 168-171 (DNTV) substituted with DPAGC (Novamyl loop with adjustments in last part) |

Further, amino acid alterations were combined as follows:

| Alteration with insertion in SEQ ID NO: 2 | Substitutions in SEQ ID NO: 2 |
|---|---|
| | D233G + G234D |
| | Q35K + Y75F + D168Y |
| | Q35R + Y75F |
| | Q35R + Y75F + D168Y |
| 168-171 (DNTV) substituted with DPAGF | Y75A |
| 168-171 (DNTV) substituted with DPAGF | Q35K + Y75A |
| 168-171 (DNTV) substituted with DPAGF | Q35K + Y75A + D233G + G234D |
| 168-171 (DNTV) substituted with DPAGF | Y75A + G234D |
| 168-171 (DNTV) substituted with DPAGF | Y75A + D233G + G234D |
| 166-171 (LGDNTV) substituted with FTDPAGF | Y75A |
| 166-171 (LGDNTV) substituted with FTDPAGF | Q35K + Y75A |
| 166-171 (LGDNTV) substituted with FTDPAGF | Q35K + Y75A + D233G + G234D |

Example 2

Construction of Variants of Acid Amylase from *A. niger*

The three-dimensional structure 2AAA for the acid alpha-amylase from *Aspergillus niger* (SEQ ID NO: 3) was compared with the structure of Novamyl 1QHO, and variants were constructed by altering the sequence SEQ ID NO: 3 as follows:
Q35K
Q35R
P70K
L151F
L151D
N233G+G234D
D75G
D75A
166-171 (EGDTIV) substituted with FTDPAGF (Novamyl loop (long))

Example 3

Construction of Variants of Fungal Amylase from *T. lanuginosus*

A three-dimensional model of SEQ ID NO: 4 (fungal amylase from *T. lanuginosus*) was constructed from a model of SEQ ID NO: 2 (fungal amylase from *A. oryzae*) using the alignment shown in FIG. 1. Residues were selected, and variants were constructed with amino acid alterations to substitute or delete selected residues as follows:
G35K
G35R
A76del+D77del
D74del+A78del
D74A
D74G
D77A
D77G
Y157W
L168F+A169T+T171P+P172A+T173G

Example 4

Anti-Staling Effect of Variants (Straight-Dough Method)

Baking tests were made with the following variants of SEQ ID NO: 2 (fungal amylase from *A. oryzae*):

| Alteration in SEQ ID NO: 2 (fungal amylase) |
|---|
| 168-171 (DNTV) substituted with DPAGF |
| Y75A |
| Q35R |
| Q35R + Y75F |
| 168-171 (DNTV) substituted with DPAGC |
| L232Y |
| 168-171 (DNTV) substituted with DPAGF + Y75A |
| D233G + G234D |
| 168-171 (DNTV) substituted with DPAGF + Q35K + Y75A |

Doughs were made according to the straight dough method. Bread was baked in lidded pans, and the bread was stored at ambient temperature. Firmness and elasticity were evaluated after 1, 4 and 6 days. Each variant was added at a dosage of 1 mg per kg flour. Controls were made without enzyme, with the parent fungal amylase of SEQ ID NO: 2 and with Novamyl (maltogenic alpha-amylase of SEQ ID NO: 1).

The results showed that the fungal alpha-amylase variants and Novamyl improved the elasticity after storage compared to the control without enzyme, whereas the fungal alpha-amylase gave a slightly lower elasticity. All the enzymes tested (variants, fungal amylase and Novamyl) improved the firmness after storage. In conclusion, the amino acid alterations succeeded in changing the functional properties of the fungal amylase to make it more Novamyl-like.

Example 5

Anti-Staling Effect of Variants (Sponge-and-Dough Method)

Baking tests were made with the following variants of SEQ ID NO: 2 (fungal amylase from *A. oryzae*):

| Alteration in SEQ ID NO: 2 (fungal amylase) |
|---|
| 168-171 (DNTV) substituted with DPAGF |
| Y75A |

Doughs were made by the sponge & dough method, and the variants were tested as in the preceding example. Controls were made without enzyme, with the parent fungal amylase of SEQ ID NO: 2 and with Novamyl (maltogenic alpha-amylase of SEQ ID NO: 1).

The variants show comparable softness and improved elasticity relative to the parent amylase, when dosed at optimal dosage in this trial.

A sensory evaluation by a small panel agrees with NMR data on mobility of free water and shows that the variants improve the moistness of bread crumb to the same level or slightly better than the parent amylase.

In conclusion, the variants showed improved effect (a more Novamyl-like effect) compared to the parent amylase.

Example 6

Exo/Endo Ratio of *A. oryzae* Amylase variants

The following variants of SEQ ID NO: 2 (fungal amylase from *A. oryzae*) were tested:

| Alteration in SEQ ID NO: 2 |
| --- |
| 168-171 (DNTV) substituted with DPAGF |
| Y75A |
| 168-171 (DNTV) substituted with DPAGC |
| Q35R |
| Q35R + Y75F |

The exo- and endo-amylase activities were determined for each variant by the assays described in the specification, and the parent amylase was tested for comparison. The results showed that each variant had a higher degree of exo-amylase activity (higher exo/endo-amylase ratio) that the parent fungal amylase.

Example 7

Exo/Endo Ratio of *A. niger* Amylase Variants

The following variants of SEQ ID NO: 3 (acid amylase from *A. niger*) were tested:

| Alteration in SEQ ID NO: 3 |
| --- |
| D75G |
| Q35K |
| L151F |
| L151D |
| N233G + G234D |

The exo- and endo-amylase activities were determined for each variant by the assays described in the specification, and the parent amylase was tested for comparison. The results showed that each variant had a higher degree of exo-amylase activity (higher exo/endo-amylase ratio) that the parent fungal amylase.

---

The invention claimed is:

1. An isolated variant polypeptide of a parent fungal alpha-amylase which:
 a) has an amino acid sequence having at least 95% identity to SEQ ID NO: 2;
 b) compared to SEQ ID NO: 2 comprises an amino acid alteration which is a deletion, substitution or insertion at a position corresponding to 168-171;
 c) has the ability to hydrolyze starch; and
 d) has improved anti-staling effect in baked products compared with the parent.

2. The polypeptide claim 1, wherein the alteration comprises substitution or insertion with an amino acid residue of the same type as the corresponding residue in SEQ ID NO: 2 sequence, wherein the type is positively charged, negatively charged, hydrophilic or hydrophobic.

3. The polypeptide of claim 1, wherein the alteration comprises substitution or insertion with a larger or smaller amino acid residue depending on whether the corresponding residue in SEQ ID NO: 2 sequence is larger or smaller.

4. The polypeptide of claim 1, comprising an alteration N169P, T170A, 168-171 (DNTV) substituted with DPAGF, 168-171 (DNTV) substituted with DPAGL, or 168-171 (DNTV) substituted with DPAGC.

5. The polypeptide of claim 1, which has the amino acid sequence of SEQ ID NO: 2 with one of the following sets of alterations:

N169P
T170A
168-171 (DNTV) substituted with DPAGF
168-171 (DNTV) substituted with DPAGL
168-171 (DNTV) substituted with DPAGC -continued 168-171 (DNTV) substituted with DPAGF + Y75A
168-171 (DNTV) substituted with DPAGF + Q35K + Y75A
168-171 (DNTV) substituted with DPAGF + Q35K + Y75A + D233G + G234D
168-171 (DNTV) substituted with DPAGF + Y75A + G234D
168-171 (DNTV) substituted with DPAGF + Y75A + D233G + G234D.

6. A process for preparing a dough or a baked product from dough comprising adding the polypeptide of claim 1 to the dough.

7. The process of claim 6, further comprising adding an additional enzyme, which is a second amylase, a protease, a peptidase, a transglutaminase, a lipolytic enzyme, a cellulase, a xylanase, an oxidoreductase, and/or a carbohydrate oxidase.

* * * * *